US010960283B2

(12) United States Patent
Murdock et al.

(10) Patent No.: US 10,960,283 B2
(45) Date of Patent: Mar. 30, 2021

(54) SMART SYSTEM FOR DISPLAY OF DYNAMIC MOVEMENT PARAMETERS IN SPORTS AND TRAINING

(75) Inventors: Wilbert Quinc Murdock, Bronx, NY (US); Philip Alister Williams, Salt Point, NY (US)

(73) Assignees: Wilbert Quinc Murdock, Bronx, NY (US); Philip Alister Williams, Salt Point, NY (US)

( * ) Notice: Subject to any disclaimer, the term of this patent is extended or adjusted under 35 U.S.C. 154(b) by 545 days.

(21) Appl. No.: 12/799,520

(22) Filed: Apr. 26, 2010

(65) Prior Publication Data
US 2011/0281621 A1 Nov. 17, 2011

Related U.S. Application Data

(62) Division of application No. 09/570,233, filed on May 12, 2000, now Pat. No. 7,789,742.

(51) Int. Cl.
A63B 69/36 (2006.01)
A63B 24/00 (2006.01)
(Continued)

(52) U.S. Cl.
CPC ............ *A63B 69/36* (2013.01); *A61B 5/0205* (2013.01); *A61B 5/11* (2013.01); *A61B 5/6895* (2013.01);
(Continued)

(58) Field of Classification Search
CPC . A63B 24/0021; A63B 24/0084; A63B 67/02; A63B 67/36; A63B 67/3632;
(Continued)

(56) References Cited

U.S. PATENT DOCUMENTS 3,792,863 A * 2/1974 Evans ................ A63B 69/3632
340/669
4,898,389 A 2/1990 Plutt
(Continued)

*Primary Examiner* — William H McCulloch, Jr.

(57) ABSTRACT

A system that wirelessly integrates actual game equipment with a computer and the internet to allow players remotely located from one another to play a competitive real or simulated game of golf. An individual player may opt to play solo or practice to improve basic golfing techniques. The system includes smart golf clubs, a golf ball receptacle, and a golf club motion sensing devices, all containing circuits, contact and or noncontact motion sensors coupled with signal processing and radio frequency transmitter circuitry to wirelessly communicate game performance information to a remote receiver-computer. The computer displays player information and visually simulates and controls a game between one or more local players or via the internet having similar equipment and remotely located from each other. Standard golf clubs may be retrofitted with the sensors and associated circuitry to convert such clubs into "smart clubs" for use with the system. The system employs specially developed computer software to process player performance data, control game play, communicate game information between players, generate and control visual simulations, and display player performance information and dynamic motion parameters.

20 Claims, 14 Drawing Sheets

(51) Int. Cl.
| | |
|---|---|
| *A63B 67/02* | (2006.01) |
| *A63F 13/21* | (2014.01) |
| *A63F 13/79* | (2014.01) |
| *A63F 13/812* | (2014.01) |
| *A63F 13/87* | (2014.01) |
| *A63B 57/40* | (2015.01) |
| *A63F 13/211* | (2014.01) |
| *A63F 13/212* | (2014.01) |
| *A63F 13/245* | (2014.01) |
| *A63F 13/35* | (2014.01) |
| *A63B 63/00* | (2006.01) |
| *G16H 40/67* | (2018.01) |
| *A61B 5/0205* | (2006.01) |
| *A61B 5/11* | (2006.01) |
| *A61B 5/00* | (2006.01) |
| *G06Q 10/06* | (2012.01) |
| *G09B 19/00* | (2006.01) |
| *G01S 19/26* | (2010.01) |
| *A63B 71/06* | (2006.01) |
| *A63B 57/30* | (2015.01) |
| *A63B 53/04* | (2015.01) |
| *G01S 19/19* | (2010.01) |
| *A63F 9/24* | (2006.01) |

(52) U.S. Cl.
CPC .......... *A61B 5/744* (2013.01); *A63B 24/0006* (2013.01); *A63B 24/0021* (2013.01); *A63B 24/0084* (2013.01); *A63B 57/405* (2015.10); *A63B 67/02* (2013.01); *A63B 69/3614* (2013.01); *A63F 13/21* (2014.09); *A63F 13/211* (2014.09); *A63F 13/212* (2014.09); *A63F 13/245* (2014.09); *A63F 13/35* (2014.09); *A63F 13/79* (2014.09); *A63F 13/812* (2014.09); *A63F 13/87* (2014.09); *G01S 19/26* (2013.01); *G06Q 10/0639* (2013.01); *G09B 19/0038* (2013.01); *G16H 40/67* (2018.01); *A61B 5/1121* (2013.01); *A61B 5/1127* (2013.01); *A61B 5/1128* (2013.01); *A61B 5/745* (2013.01); *A61B 2503/10* (2013.01); *A63B 24/0062* (2013.01); *A63B 24/0075* (2013.01); *A63B 53/04* (2013.01); *A63B 57/357* (2015.10); *A63B 57/40* (2015.10); *A63B 63/00* (2013.01); *A63B 69/362* (2020.08); *A63B 69/3632* (2013.01); *A63B 69/3655* (2013.01); *A63B 69/3658* (2013.01); *A63B 69/3676* (2013.01); *A63B 69/3685* (2013.01); *A63B 69/3688* (2013.01); *A63B 71/0616* (2013.01); *A63B 71/0622* (2013.01); *A63B 71/0669* (2013.01); *A63B 71/0686* (2013.01); *A63B 2024/0034* (2013.01); *A63B 2024/0037* (2013.01); *A63B 2024/0056* (2013.01); *A63B 2024/0068* (2013.01); *A63B 2071/063* (2013.01); *A63B 2071/065* (2013.01); *A63B 2071/0647* (2013.01); *A63B 2220/00* (2013.01); *A63B 2220/13* (2013.01); *A63B 2220/16* (2013.01); *A63B 2220/30* (2013.01); *A63B 2220/53* (2013.01); *A63B 2220/62* (2013.01); *A63B 2220/801* (2013.01); *A63B 2220/803* (2013.01); *A63B 2220/833* (2013.01); *A63B 2220/89* (2013.01); *A63B 2225/20* (2013.01); *A63B 2225/50* (2013.01); *A63F 9/24* (2013.01); *G01S 19/19* (2013.01)

(58) Field of Classification Search
CPC ............ A63B 67/3655; A63B 67/3676; A63B 67/3685; A63B 67/3688; A63B 71/0616; A63B 2220/83; A63B 2220/833
See application file for complete search history.

(56) References Cited

U.S. PATENT DOCUMENTS

| | | | |
|---|---|---|---|
| 5,056,783 A | 10/1991 | Matcovich et al. | |
| 5,056,791 A | 10/1991 | Poillon | |
| 5,128,671 A | 7/1992 | Thomas, Jr. | |
| 5,209,483 A * | 5/1993 | Gedney | A63B 69/0026 473/223 |
| 5,245,537 A | 9/1993 | Barber | |
| 5,365,799 A | 11/1994 | Okada | |
| 5,374,063 A | 12/1994 | Ogden | |
| 5,390,927 A | 2/1995 | Angelos | |
| 5,395,116 A | 3/1995 | Blaakman | |
| 5,435,561 A | 7/1995 | Conley | |
| 5,447,305 A | 9/1995 | Socci | |
| 5,611,731 A | 3/1997 | Bouton | |
| 5,616,832 A | 4/1997 | Nauck | |
| 5,700,204 A * | 12/1997 | Teder | A63B 24/0021 473/199 |
| 5,702,323 A | 12/1997 | Poulton | |
| 5,707,298 A | 1/1998 | Chovanes | |
| 5,709,610 A | 1/1998 | Ognajanovic | |
| 5,779,549 A | 7/1998 | Walker et al. | |
| 5,792,000 A | 8/1998 | Weber | |
| 5,826,578 A | 10/1998 | Curchod | |
| 5,826,874 A | 10/1998 | Teitell et al. | |
| 5,830,069 A | 11/1998 | Soltesz et al. | |
| 5,830,077 A | 11/1998 | Yavitz | |
| 5,884,913 A * | 3/1999 | Cohen | A63B 69/3694 340/323 R |
| 5,902,968 A | 5/1999 | Sato | |
| 5,906,547 A | 5/1999 | Tynan | |
| 5,982,352 A | 11/1999 | Pryor | |
| 6,073,086 A * | 6/2000 | Marinelli | A63B 43/00 473/198 |
| 6,162,123 A | 12/2000 | Woolston | |
| 6,254,492 B1 * | 7/2001 | Taggett | A63B 24/0003 473/219 |
| 6,537,076 B2 * | 3/2003 | McNitt | A63B 24/0003 434/247 |
| 7,095,312 B2 * | 8/2006 | Erario | A63B 24/0021 340/323 R |
| 7,321,330 B2 * | 1/2008 | Sajima | A63B 24/0021 342/118 |
| 7,691,004 B1 * | 4/2010 | Lueders | A63B 53/04 473/222 |
| 7,789,742 B1 * | 9/2010 | Murdock | A63B 24/0021 463/3 |
| 7,789,767 B2 * | 9/2010 | Lindsay | A63B 24/0021 473/150 |
| 8,002,645 B2 * | 8/2011 | Savarese | A63B 24/0021 473/155 |
| 8,032,324 B1 * | 10/2011 | Bryant | G01C 17/02 702/141 |
| 8,253,586 B1 * | 8/2012 | Matak | H04Q 9/00 340/870.07 |
| 8,257,189 B2 * | 9/2012 | Koudele | A63B 43/00 473/155 |
| 8,425,350 B2 * | 4/2013 | Savarese | A63B 24/0021 156/145 |
| 9,028,338 B2 | 5/2015 | Chiono | |
| 9,662,558 B2 * | 5/2017 | Murdock | A63B 67/02 |
| 9,802,129 B2 * | 10/2017 | Murdock | A63B 69/3632 |
| 10,137,347 B2 * | 11/2018 | Thornton | A63B 53/0466 |
| 10,159,885 B2 * | 12/2018 | Thornton | A63B 53/0466 |
| 10,220,285 B2 * | 3/2019 | Thornton | A63B 69/36 |
| 10,226,681 B2 * | 3/2019 | Thornton | A63B 24/0003 |
| 10,500,452 B2 * | 12/2019 | Wallans | A63B 53/047 |
| 10,737,165 B2 * | 8/2020 | Murdock | A63B 24/0084 |
| 2002/0036617 A1 | 3/2002 | Pryor | |
| 2004/0142766 A1 * | 7/2004 | Savarese | A63B 24/0021 473/353 |

(56) References Cited

U.S. PATENT DOCUMENTS

| | | | | |
|---|---|---|---|---|
| 2005/0171410 A1* | 8/2005 | Hjelt | ............... | A61B 5/00 600/300 |
| 2007/0167247 A1* | 7/2007 | Lindsay | ............ | A63B 24/0021 473/131 |
| 2008/0076580 A1* | 3/2008 | Murdock | ........... | A63B 24/0021 463/42 |
| 2008/0188310 A1* | 8/2008 | Murdock | ........... | A63B 69/3632 463/42 |
| 2011/0081978 A1* | 4/2011 | Murdock | ........... | A63B 24/0021 473/191 |
| 2011/0082571 A1* | 4/2011 | Murdock | ........... | A63B 24/0021 700/92 |
| 2011/0087344 A1* | 4/2011 | Murdock | ........... | A63B 24/0021 700/91 |
| 2011/0092260 A1* | 4/2011 | Murdock | ........... | A63B 24/0021 463/3 |
| 2011/0130223 A1* | 6/2011 | Murdock | ........... | A63B 24/0021 473/409 |
| 2011/0151977 A1* | 6/2011 | Murdock | ........... | A63B 24/0021 463/42 |
| 2011/0212757 A1* | 9/2011 | Murdock | ........... | A63B 24/0021 463/2 |
| 2011/0281621 A1* | 11/2011 | Murdock | ........... | A63B 24/0021 463/3 |
| 2012/0220385 A1* | 8/2012 | Richardson | ........ | A63B 24/0021 473/156 |
| 2014/0297007 A1* | 10/2014 | Voutilainen | ........ | A63B 24/0003 700/91 |
| 2016/0354660 A1* | 12/2016 | Kostuj | ............... | G09B 19/0038 |
| 2016/0361592 A1* | 12/2016 | Isogawa | ............ | G06K 9/00342 |
| 2017/0004729 A1* | 1/2017 | Kano | ................. | G09B 19/0038 |
| 2017/0282081 A1* | 10/2017 | Murdock | ............. | A63B 57/405 |
| 2018/0065017 A1* | 3/2018 | Murdock | ........... | A63B 24/0084 |
| 2018/0117438 A1* | 5/2018 | Murdock | ........... | A63B 69/3614 |

* cited by examiner

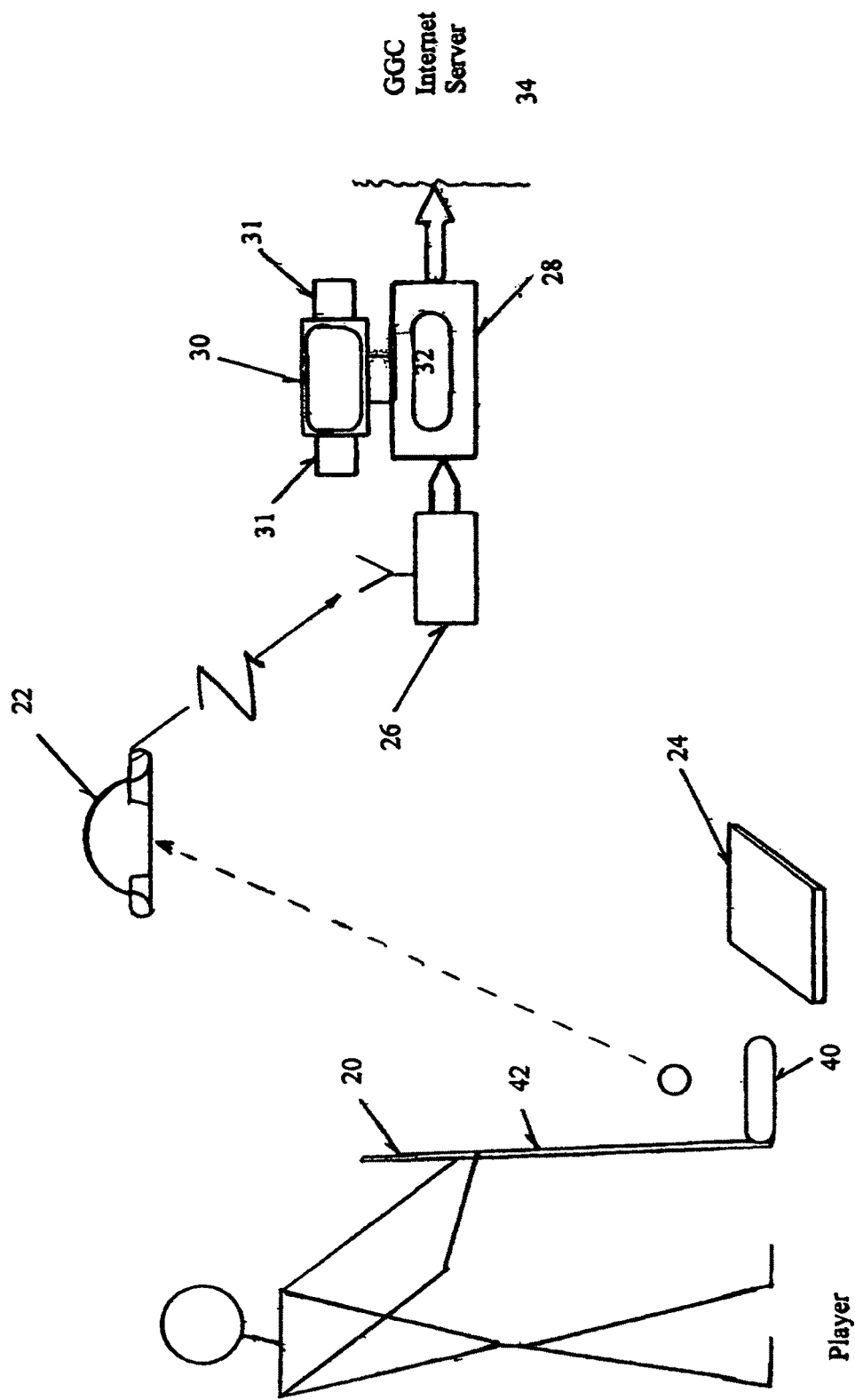
FIGURE: 1

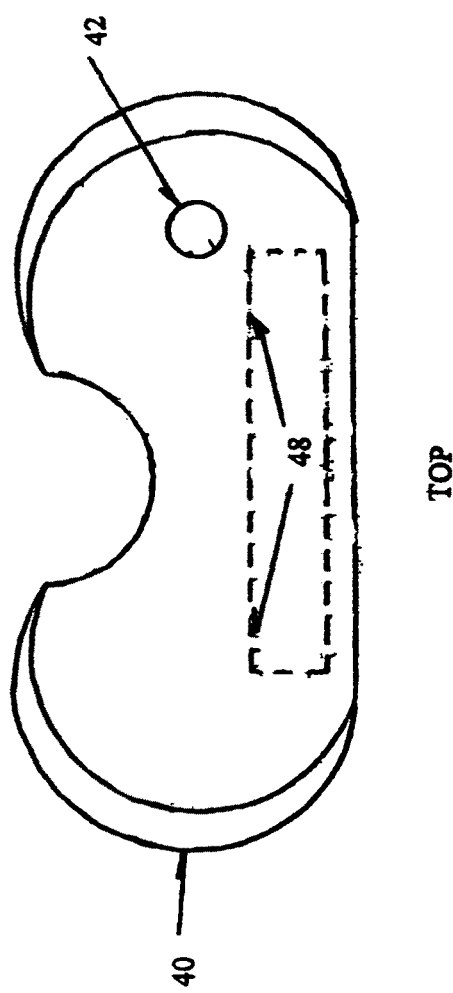
FIGURE: 2
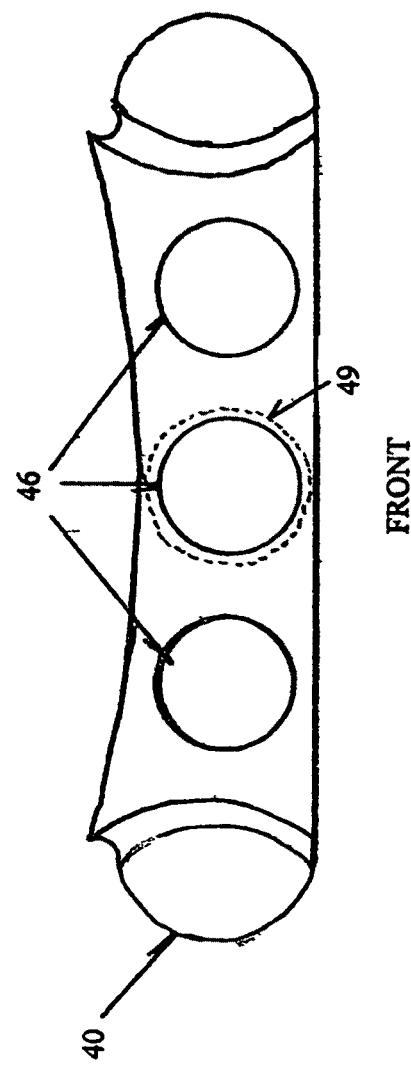
FIGURE: 3

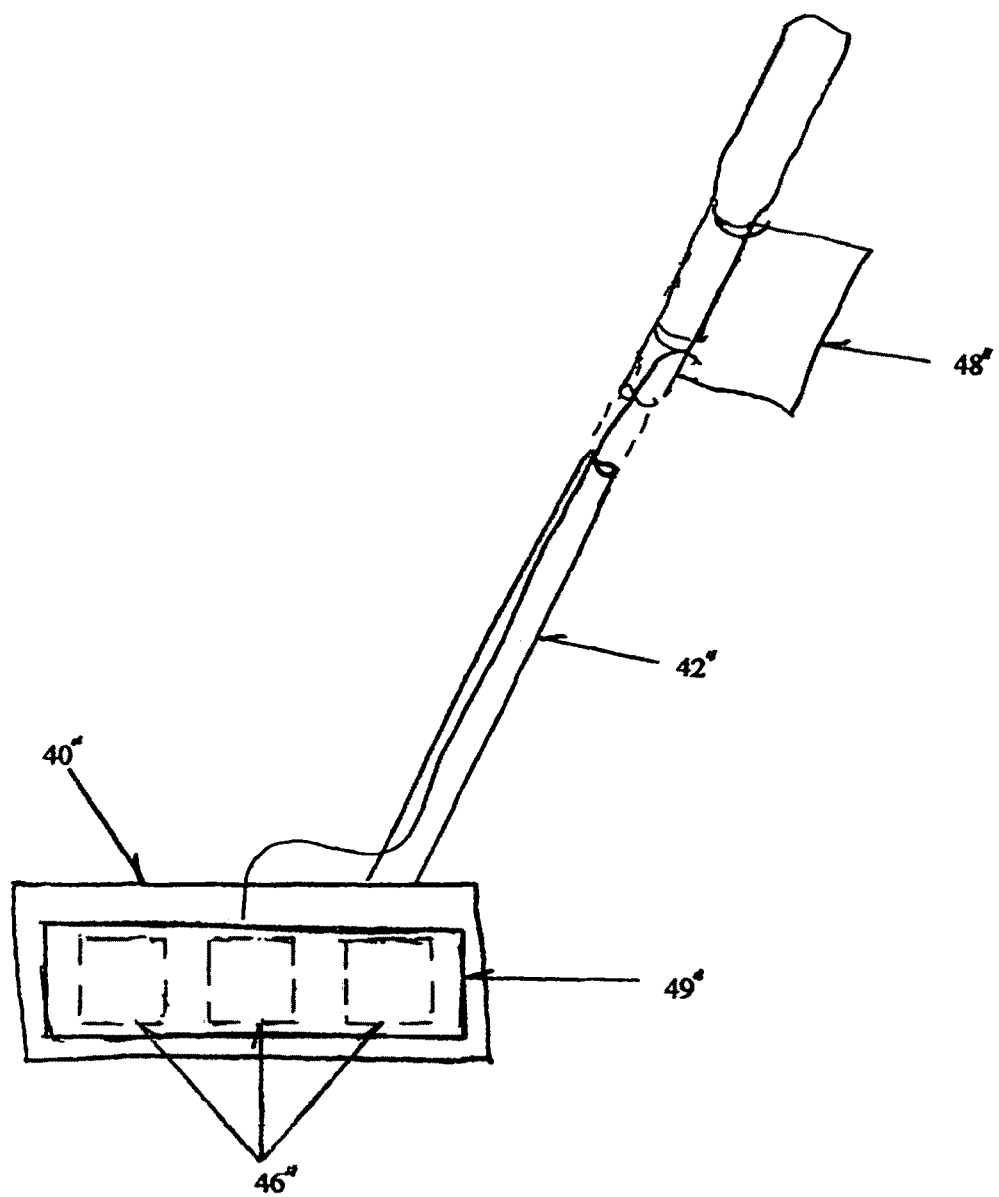
FIGURE: 4

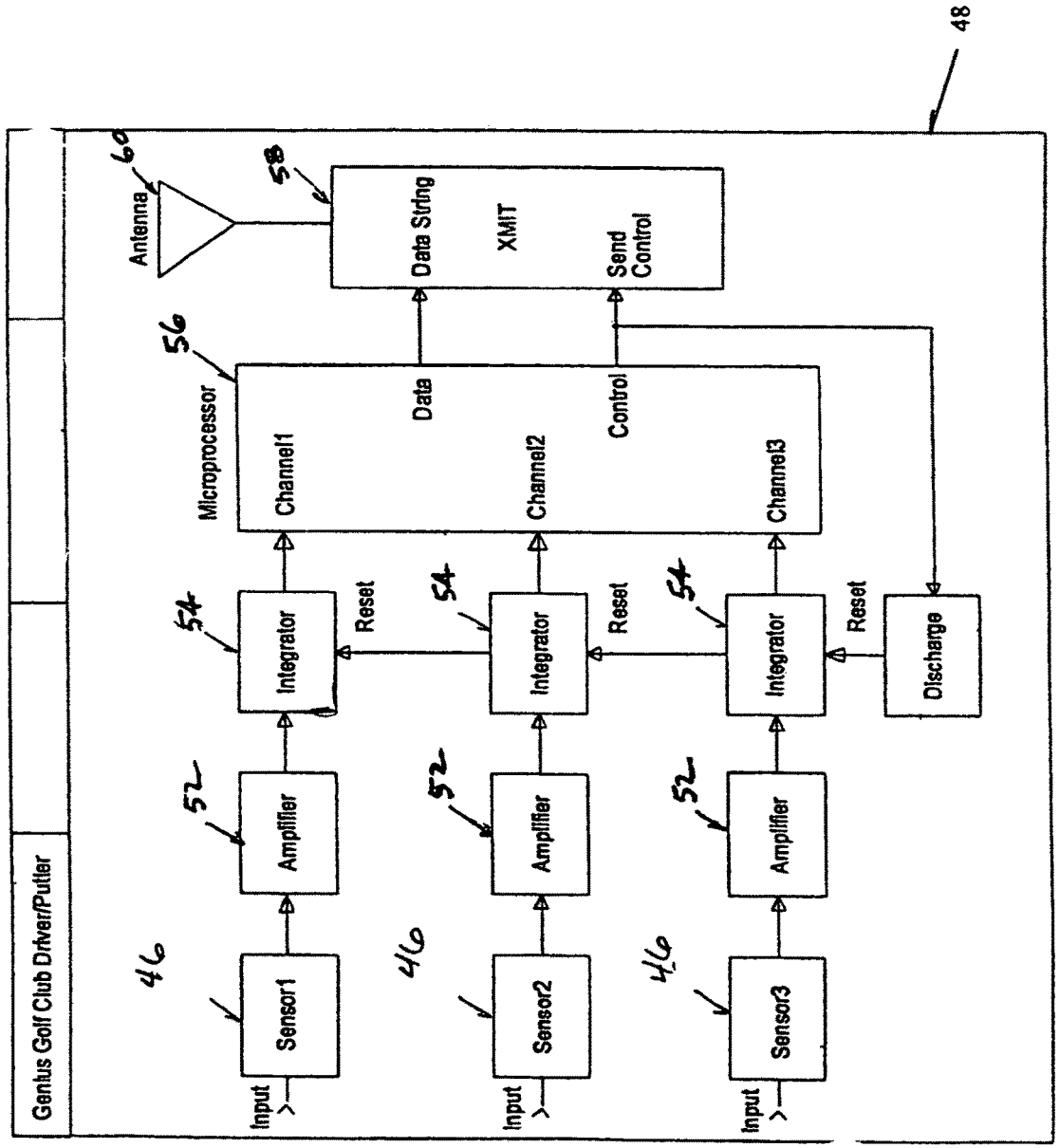
FIGURE: 5

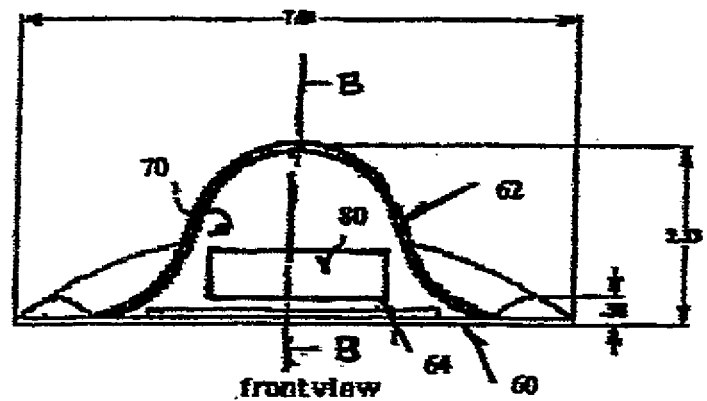
front view
back view
FIGURE: 6A

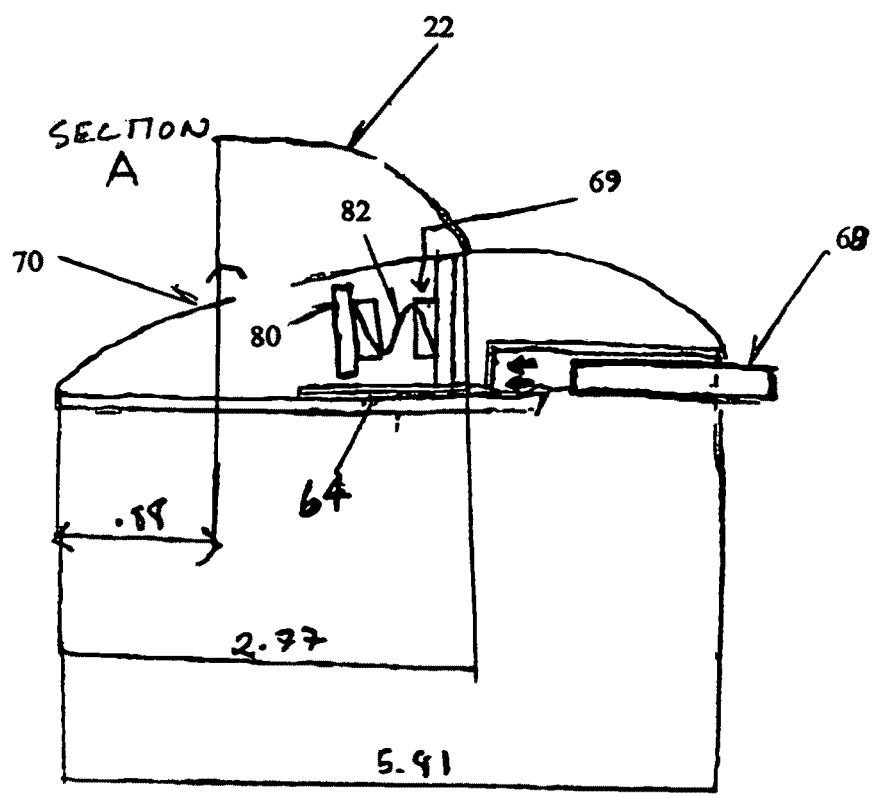
FIGURE: 6B

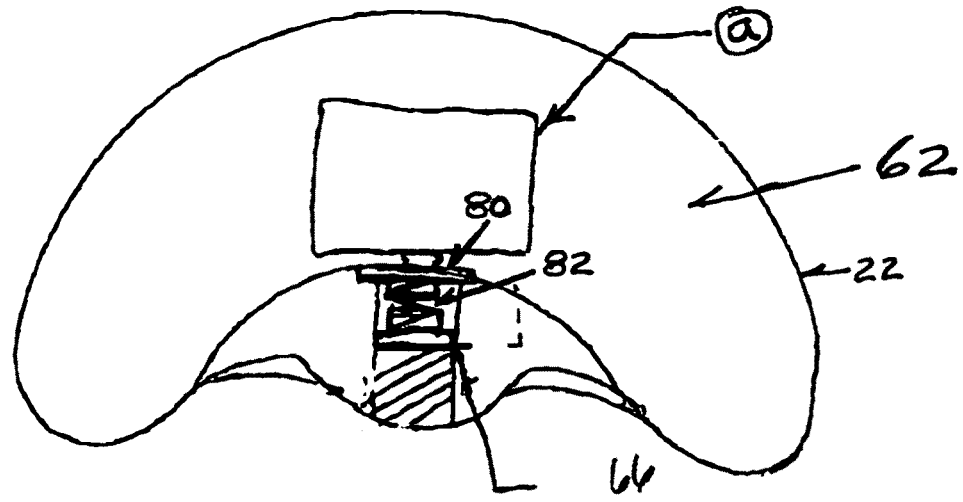
Top view with components exposed
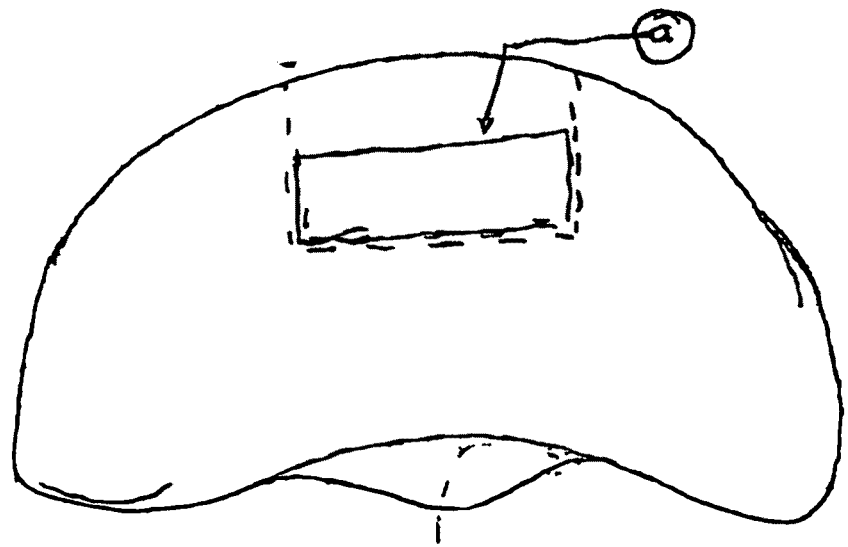
ⓐ Bottom view with electronics in position
FIGURE: 6C

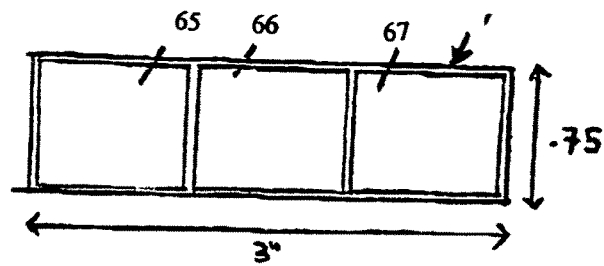
Tripad Sensor with three different activation areas.
FIGURE: 7

SMART SYSTEM FOR DISPLAY OF DYNAMIC MOVEMENT PARAMETERS IN SPORTS AND TRAINING

CROSS REFERENCE TO RELATED APPLICATION

Priority is claimed from U.S. Provisional Application Ser. No. 60/133,722, filed May 12, 1999 for all subject matter common hereto. That provisional application is incorporated by reference herein. This is a divisional application and the parent application for this divisional application is Ser. No. 09/570,233.

REFERENCE TO MICROFICHE APPENDIX

A microfiche appendix including 1 microfiche with 27 frames accompanies and forms a part of this application.

FIELD OF INVENTION

This invention relates to a smart game system coupling real sports equipment and a computer. More particularly, this invention relates to a system wherein a golf club or sports item communicates dynamic contact and movement parameters wirelessly to a personal computer and thereby, if desired, to the internet.

BACKGROUND OF THE INVENTION

Resolving an object's direction post impact is a problem that has been addressed in the literature often with great complexity. In addition, few high-tech solutions have been employed but may be unsuitable for use under repeated impact of the object and impact surface.

A number of patented sports implements such as golf club devices embody various ball contact or club swing sensing components. Typically, these devices display information related to a golf player's swing and accuracy in hitting a golf ball. In certain of these, the information is displayed or signaled by some of the golf club itself in the form of a small visual readout or an audible sound. One such device contains an array of mechanically depressible pins on the face of the golf club. When the ball is struck by the club, the pins are physically depressed in a pattern to inform the player of the location on the club face where contact with the ball occurred. Another device uses a light emission and reflection detection technique to provide a player's information, displayed on the club, regarding the alignment of the golf ball with the preferred location on the golf club face.

Also, numerous conventional computer golf game software packages and video games use a variety of unrealistic techniques to emulate the striking of a golf ball with a club. None of these correlate with actual golf clubs, actual golf ball target or cup receptacles, or a swing detector that senses the actual golf stroke.

It is desirable to remotely communicate actual player performance and location, whereby more sophisticated analysis and prediction possibilities are realizable via computer technology and state-of-the-art display techniques. Further, it is also desirable to use such performance information in an expanded capacity to provide interactive competitive game play among numerous players in locations remote from each other.

SUMMARY OF INVENTION

This invention relates to a system that interconnects real golf or other sports equipment to a computer. In a preferred embodiment the computer is coupled wirelessly to a golf club, a receptacle, or a swing sensing component. Hereon, sports implements and or gaming items are examples of a sports equipment, item, tool, or unit, and the latter should be understood to be included in the former. Further, the invention, with components summarized below, allows one or more players to enter into a competition against each other. Each player asks the computer who is available to play a contest. Once a player pairs up against another player anywhere in the world and play ensues, the computer display screens show each participant's score via animation or graphics that preferably relate to a player's individual performance statistics. A single player may play without an opponent to practice and improve basic sports such as golfing skills using the computer and display to track performance.

The system application is unlimited. Much of this system can be used not only for golfing competition on the Internet, but for other sports as well. Sports implements other than golf clubs, swing detectors and receptacles, can be outfitted with sensors according to this invention and used for training purposes, rehab, or for interactive internet game competition. Standard golf clubs or sports implements may be retrofitted with the sensors and associated circuitry to convert such clubs or implements into "smart clubs" or smart sports implements for use with the system.

The technology can also be used for training, competition, and the improvement of player reflexes and coordination. With little or no modification, the technology also has applications in medicine, particularly physical therapy.

1. Smart Golf Club

A wireless golf club is constructed to contain, or alternatively, a standard golf club is modified to contain a multiple sensor or transducer array located on the club head at the face or hitting surface. Upon impact of the head of the club with a golf ball, the impacted sensors produce detectable variances representing the magnitude and duration of the club-ball impact force and impulse and the proximate location of such contact relative to the preferred location, the "sweet spot", on the face of the club head. The variances are electronically processed into digitally coded information and remotely transmitted by an electrical communication circuit either contained within or attached to the golf club.

In each golf club device and golf ball receptacle device according to this invention, in a preferred embodiment, the transducers are or include piezo-active elements and or pressure sensors. As used herein, "piezo-active" includes piezoelectric and piezoresistive components. Piezo-active components are defined as components with the electrical properties of which, when the component is subjected to physical force, vary. Moreover, in another preferred embodiment the sensors are micro sensors to detect and derive angle and direction information data between an object or game projectile and the sports implement. Micro sensors are miniature electronic devices that detect information about a specific variable, such as temperature or light.

The smart golf club system uses biofeedback to create an intelligent golf training and entertainment system. The smart golf club system is a diagnostic and analysis tool used to improve a player's skills by relatively instantaneous visual cues and acoustic feedback with little or no human intervention. The smart golf club system takes the generated data and reconstructs it into a useful visual format that can be presented in a variety of ways including 3-dimensional animation.

The smart golf club system integrated circuit or circuits can be located anywhere within the club including the head and or shaft.

The smart golf club has a means via its built in microcontroller to process, analyze, store, hitting pattern data and transmit it to the computer and or the Internet for further analysis. In playback mode the smart golf club system memorizes the number of times each sensor was struck. This provides the golfer information about his or her hitting pattern. Using a computer algorithm, we can analyze and calculate a hitting pattern resulting in a personalized sports hitting detection system for each athlete. A computer or equivalently a computer processor is hereon and heretofore understood to be, and or comprise, a microcontroller and or a microprocessor, and each of the latter is understood to be included in the former.

2. Golf Ball Receptacle

The ball receptacle has an open end to receive a golf ball and contains a transducer located so as to sense the ball entering the receptacle. Upon impact with the golf ball, the sensor produces a detectable variance representing impact with the ball. The variance is electronically processed into digitally coded information and remotely transmitted by an electrical communication circuit. In one preferred embodiment the communication circuit is contained within the receptacle. Preferably, the receptacle communication circuit is a radio frequency transmitter. The receptacle can either be designed for indoor use or can be a cup in an actual green with the communication circuit housed in the cup or elsewhere conveniently located.

In each of the golf club device and golf ball receptacle device according to this invention, in a preferred embodiment, the transducers are or include piezo-active elements.

3. Motion Sensor Plate

A golf club swing motion sensing device contains an array of uniformly distributed sensing transducers upon or proximate to the device surface. This motion sensing device may be formed as a mat or a plate or other substantially flat surface from which a golf ball is hit. The transducers produce detectable varying characteristics such as capacitance representing the velocity, angle, and proximity of a golf club relative to the surface of the device. The variances are electronically processed into digitally coded information and remotely transmitted by an electrical communication circuit contained within or electronically connected to the device.

4. Wireless Signal Receiver and Computer

At each remote player site, wireless radio frequency equipment receives the digitally coded transmitted signals from the golf club, the golf ball receptacle, and the club swing motion sensing device, or a sports implement. The signals are demodulated and processed into serial binary data suitable for communications to the computer via either serial or parallel ports. As the game progresses, the computer under the control of the golfing software, monitors and directs the flow of communications between the players via the internet and displays the game simulations and performance information.

5. Computer Golfing Software System

At each remote player site, a computer under the control of the game software, monitors and controls the sequential play of the game and interacts with the local player or players at the site and also competing players at the other remote sites via the internet. The software system generates the game simulations for display and tracks each player's performance as the game progresses.

The above and further features and advantages of the invention will be better understood with reference to the accompanying drawings and the following detailed description of preferred embodiment.

BRIEF DESCRIPTION OF THE DRAWINGS

FIG. 1 is a diagrammatic illustration of components of a computer implemented game system according to this invention.

FIG. 2 is a top plan view of a golf club with sensors and circuitry used in the computer implemented system of FIG. 1.

FIG. 3 is a front elevation view of the golf club head of FIG. 2, and shows three sensors located at the face of the club head.

FIG. 4 is a diagrammatic front plan view of a putter with a club head and circuitry forming a further, alternative embodiment of a club for use with the computer implemented system of FIG. 1.

FIG. 5 is a schematic block diagram of a club head electronics installation for use with the club heads of FIGS. 2-4.

FIG. 6A is a front elevation view of a golf ball receptacle for use with the system of FIG. 1.

FIG. 6B is a cross-sectional view along the lines B-B of FIG. 6A.

FIG. 6C is a fragmentary top plan view of the receptacle of FIGS. 6A and 6B illustrating internal components of the receptacle.

FIG. 7 is a top plan view of a golf ball sensing element with three distinct activation areas for use in the receptacle of FIGS. 6A-6C.

DETAILED DESCRIPTION OF PREFERRED EMBODIMENT

1. Smart Golf Club

Figure 3A:
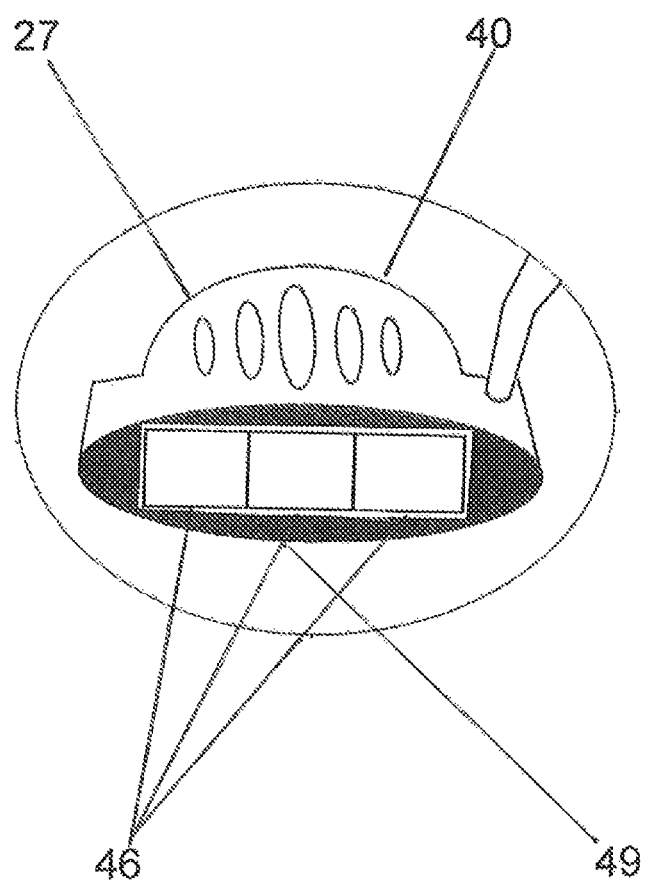
FIG. 3A is a front plan view of a further embodiment of a club head for use with the computer implemented golf system of FIG. 1.

The smart golf club 20 has a head 40 and a shaft 42. As shown in FIGS. 2 and 3, the head 40 has a shaft opening 42, a plurality of embedded contact sensors 46 (three are illustrated in the preferred embodiment), and the internal electronics circuitry 48 including a wireless radio frequency transmitter (58 in FIG. 5). As shown, at least one of the sensors 46 is located at or proximate to the optimal location on a club face 47 for contact with the golf ball, the "sweet spot" 49. The remaining two sensors are adjacent and on either side of the sweet spot 49. The contact sensors may be, but are not limited to, sensors employing piezo-active type transducers, specifically, either piezoelectric or piezoresistive transducers (similar, but is not limited to the Cooper Instruments LPM 562).

In an alternative embodiment, FIG. 3A, three sensors 46 are applied to the face of an adapted club by a Mylar tape or other means 49. Again, the electronic circuitry is internal to the club head 40 and connects to the sensors 46 by leads 27.

In a second alternative embodiment, to retrofit a standard golf club, contact sensors 46 are part of an adapter 40 attached to an ordinary club head as seen in FIG. 4 and wire connected to an electronic circuitry 48 attached to the club shaft 42 or elsewhere on the club.

A golf ball contacting any sensor 46 produces a detectable variance indication the magnitude and duration of sensor-ball impact. The variance may be a change in resistance of a micro sensor or a piezoresistive transducer or a voltage change in the case of a piezoelectric transducer. As shown in FIG. 5, the variance is detected and amplified by an associated amplifier 52 and is the input to an associated integration circuit 54, the output of which represents the energy and time duration of the ball-club contact event. Connected to the integration circuit 54, a microcontroller 56 is a multi-input signal processing circuit (similar, but not limited to a NXP MC9S08) having analog to digital signal converting circuits (ADCs), one for each input channel, and a sequential digital signal encoding circuit connected so as to convert the ADC outputs into a time multiplexed serial digital data stream containing a binary-coded word for each channel indicating the energy of the associated sensor-ball impact event.

A radio frequency transmitting circuit 58 receives the serial digital data from the microcontroller 56 and wirelessly transmits the information via an internal antenna 60 to a receiver 26 (FIG. 1) for subsequent processing by the computer 28.

2. Golf Ball Receptacle

The golf ball receptacle 22 has a top 62 shaped to allow entry of a golf ball, as shown in FIGS. 6A, 6B, and 6C. The receptacle has a contact sensor pad 64, shown in FIG. 7, containing at least one contact sensor (three different activation areas 65, 66, and 67 are illustrated in the preferred embodiment), a ball return mechanism 69 (FIG. 6B) and internal electronic circuitry 68 (FIG. 6B). The internal circuitry includes a wireless radio frequency transmitter (not separately shown in FIGS. 6A, 6B and 6C). As shown, the preferred embodiment has contact sensor pad 64 positioned within the receptacle 60 such that the center activation area 66 aligns with the center of a ball entry 70. Additional sensor activation area 65 and 67 are adjacent, one on either side of the center area 66. In the preferred embodiment, of FIGS. 6A, 6B, and 6C, and like the sensor used at the face of the club, the sensors may be, but are not limited to, sensors employing piezo-active type transducers, specifically, either piezoelectric or piezo-transducers.

Figure 8:
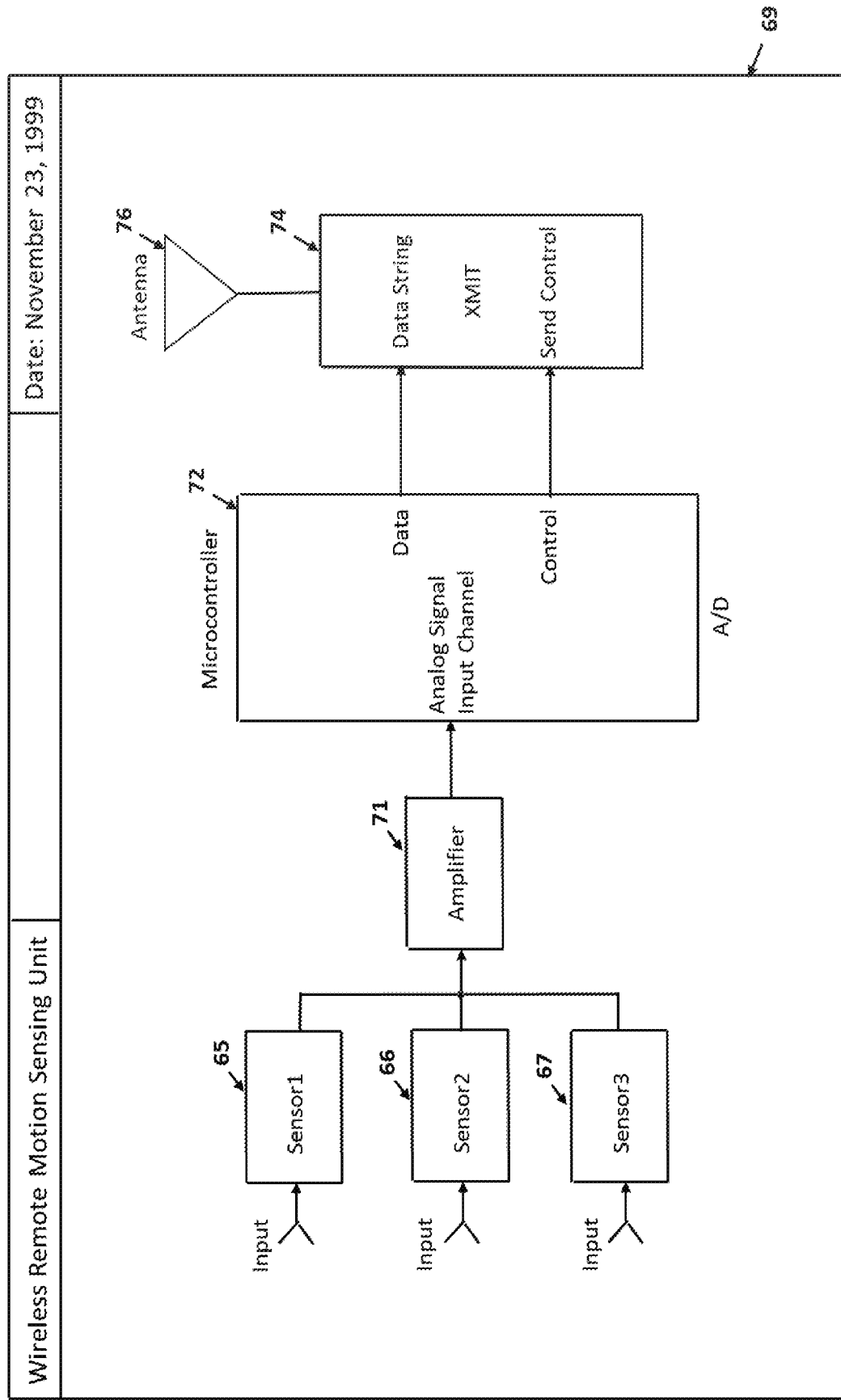
FIG. 8 is a schematic block diagram of a receptacle electronics installation for communicating with the computer in a computer implemented system according to FIG. 1.
Figure 9:
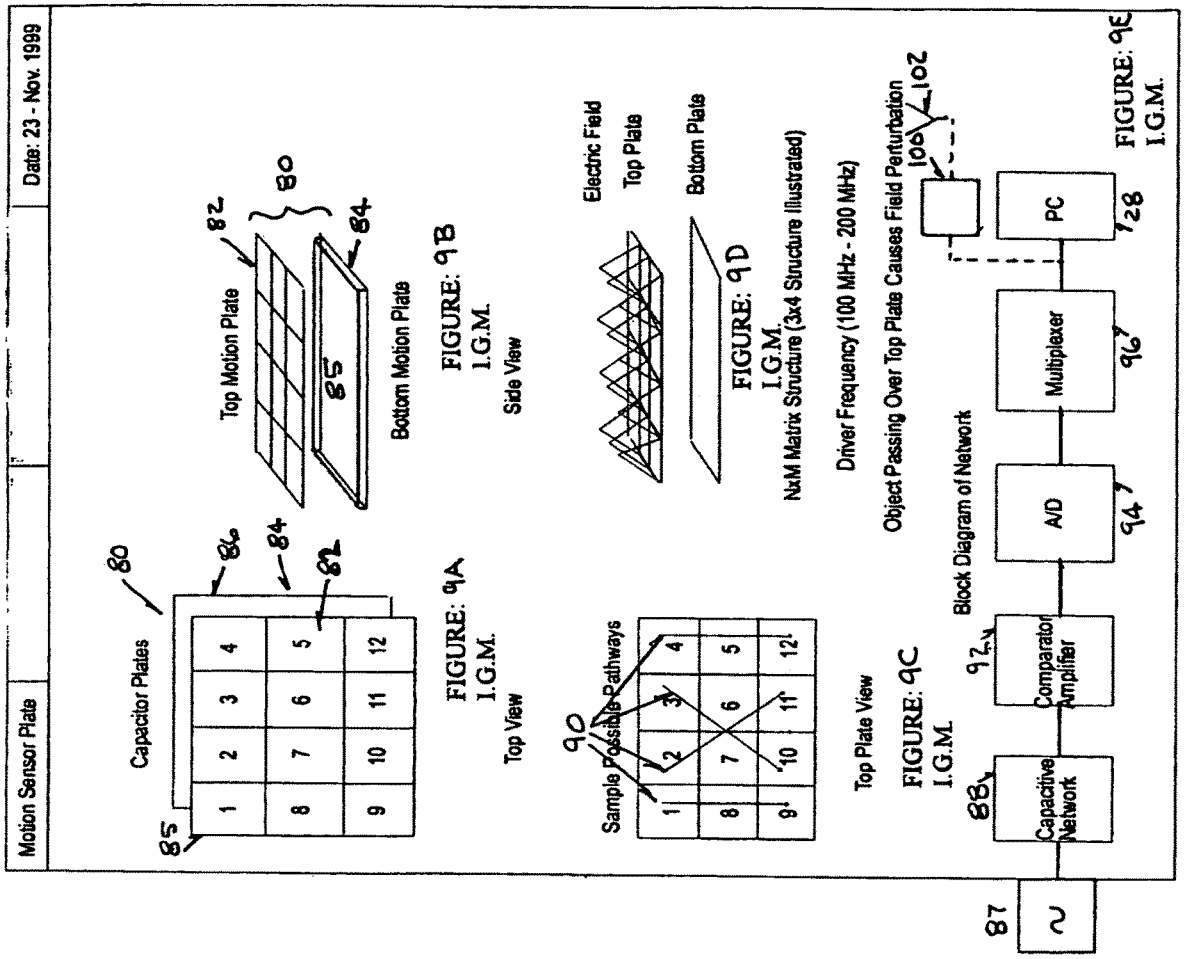
FIGS. 9A-9D, are diagrammatic illustrations of a golf club motion or swing sensor plate for use with the system according to FIG. 1.
FIG. 9E is a block diagram of electronics used in association with the swing sensor plate of FIGS. 9A-9D.

A golf ball entering the receptacle 60 and containing the sensor pad 65, 66, or 67 produces a detectable variance indicating the ball entry event. The variance may be a change in resistance in the case of a piezoresistive transducer (similar, but not limited to Cooper Instruments LPM 562) or a voltage change in the case of a piezoelectric transducer. As illustrated in FIG. 8, the variance is detected and amplified by an associated amplifier 71. The amplified signal then is input to a microcontroller 72 having an analog to digital signal converting circuit (ADC) and a digital signal encoding circuit connected so as to convert the ADC output, representing the sensors signals into a serial digital data stream containing a binary-coded word indicating the sensor-ball contact event. The microcontroller 72 may be the same or similar to the microcontroller 56 of the golf club electronics. A radio frequency transmitter circuit 74 receives the serial digital data from the microcontroller 72 and wirelessly transmits the information via an internal antenna 76 to the receiver 26 (FIG. 1) for subsequent processing by the computer 28.

The ball return mechanism 68 can be a simple back plate 80 located to be engaged by a ball entering the receptacle 22 and supported and biased by a spring or springs 82 to eject the ball. Other known ejection devices similar to those used in pinball machines and either mechanically or even electrically activated can be used to improve the effect if desired.

The receptacle configuration is susceptible to much variation. The receptacle illustrated and described above is well suited to indoor use, on carpet for example. It is clear, however, that an actual cup, installed in an actual green, with real or synthetic grass, can be similarly equipped.

3. Motion Sensor Plate

The motion sensor plate 80 having a top motion plate 82 and a bottom motion plate 84 is diagrammatically shown in FIGS. 9A-D, wherein the top motion plate 82 contains a plurality of capacitor-forming electrically isolated platelets 83 (twelve platelets are illustrated in this exemplary preferred embodiment). They are evenly distributed at or just below the top plate's exterior upper surface 82. The bottom plate 84 has a homogenous electrically conductive interior surface 85 underlying the platelets 83. Each capacitive platelet 83 contained in the top motion plate 82 forms a capacitive component when the top and bottom motion plates are vertically closely spaced to form the motion sensor plate. A suitable dielectric insulator may be sandwiched between the two plates. The structure is adhesively or otherwise mechanically joined and it may be covered or coated as desired. The result is a golf club motion sensor plate 80 containing a capacitor matrix (a 3×4 capacitor matrix is illustrated in the preferred embodiment. The capacitive components 83 are connected to form a capacitive network 88 as is indicated in FIG. 9E.

Applying an energizing high frequency alternating electrical signal having a frequency in the range from 100 MHz to 200 MHz from an oscillator 87 to the motion plate capacitive network 88 produces an electromagnetic field above the surface of each platelet 83 of the capacitive components of the motion sensor plate 80. Any object, including a golf club, passing near the surface of the energized motion plate will cause a perturbation of the electromagnetic field as illustrated by the sample possible pathways 90 across the plate in FIG. 9C. A network 92 of electrical comparator amplifiers (FIG. 9B) is connected to the capacitor network. The comparators of the network 92 are connected one-to-one with the capacitive elements of the capacitive network 88. The comparators of the network 88 detect voltage variations occasioned by the electromagnetic field disturbance due to a golf cub moving over certain of the capacitive elements of the motion plate. Each different golf club motion over the energized motion plate will produce a uniquely identifiable signal from the comparator amplifier network. There are a variety of known proximity sensors that could be gathered together in an array like that of the platelets 83 to serve as the transducer portion of the golf club and or sports implement motion detector.

The electrical signal from the comparative amplifier network 92 is applied to an analog-to-digital signal converter 94 (ADC) and the ADC digitized output signal is converted into a serial digital data stream by a multiplexer 96. This data identifies each platelet having had its field disturbed. The serial digital data can be input directly by wire from a multiplexer 96 to the computer 28 located at the site of the player and motion sensor plate 80, or as in the preferred embodiment, illustrated in FIG. 1, the serial data can be transmitted 100 and an antenna 102, included in the motion detector electronic transmitter communication circuitry from FIG. 1.

The computer 28, under the control of the game system software, will analyze the serial digital club motion signal, recognize from the transmitted signals the platelets 83 over which the club head passed and display the golf club swing motion.

The motion sensors further comprise spatial orientation devices, such as a gyro meter and an accelerometer to derive spatial orientation and or translational acceleration data, housed inside or mounted to the golf club, sports implement, or gaming item.

4. Wireless Signal Receiver and Computer

Figure 10:
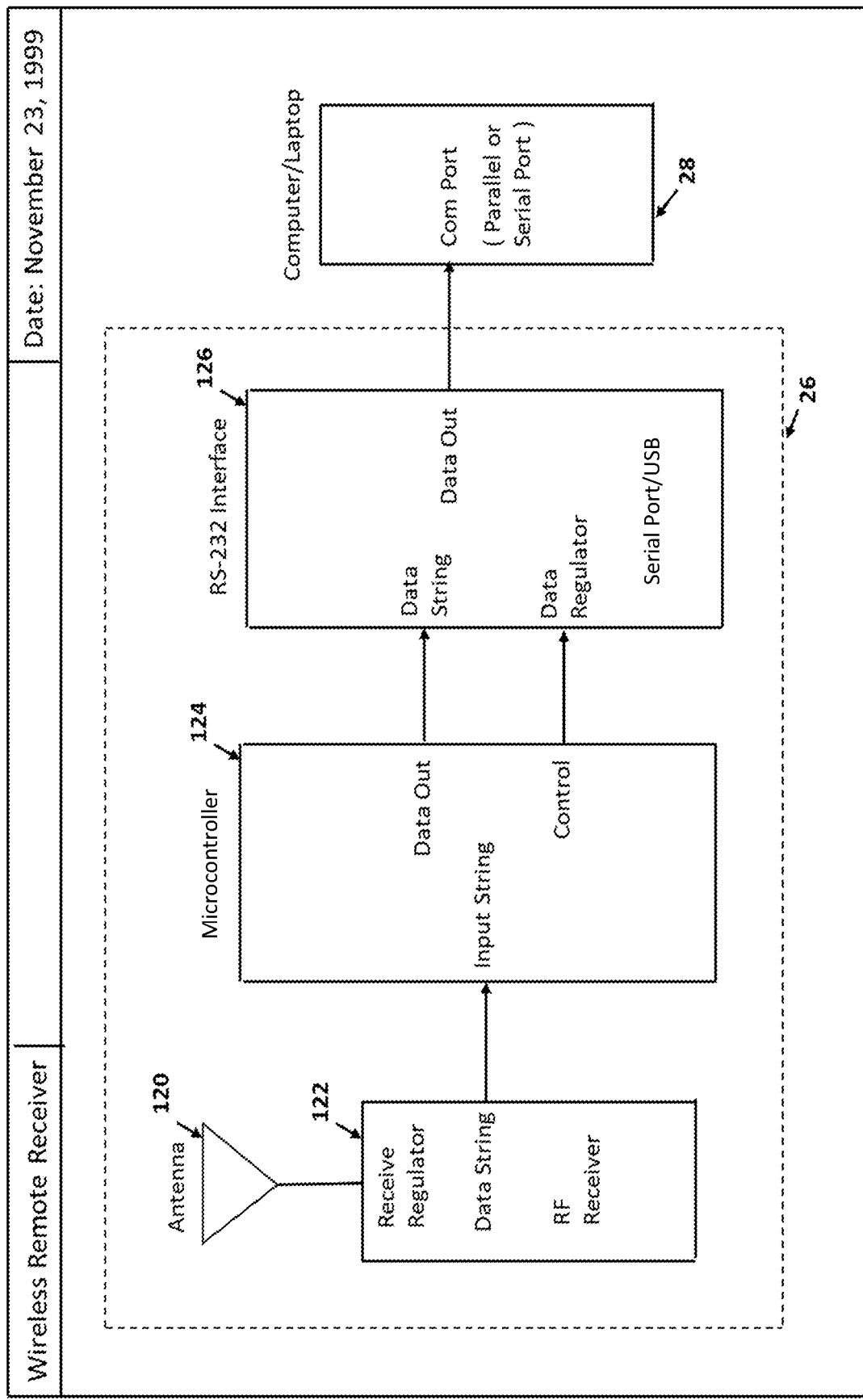
FIG. 10 is a block diagram of a receiver computer installation for use as the computer and information receiving interconnect of the system of FIG. 1.

At each player site, a wireless radio frequency signal receiver 26 is connected to the computer 28 by either the serial (USB) or parallel computer ports as shown in the functional block diagram, FIG. 10. The wireless signal receiver 26 detects digitally coded radio frequency transmissions from the communication circuit associated with any of a smart golf club 20, a golf ball receptacle 22, or a motion sensing plate 24, as shown in FIG. 1. The received transmissions are demodulated by the RF receiver circuitry 122 (FIG. 10) connected to a microcontroller 124, which converts the demodulated data signal to serial binary coded data suitable for communications to a computer 28. The computer 28, under the control of the internally installed game system software program, monitors and directs the flow of communications between remotely located players via the internet and displays the game simulations and performance information. In appropriate installations the wireless electromagnetic signals that communicate with the receiver may be infrared communications.

5. Computer Golfing Software

Figure 11:
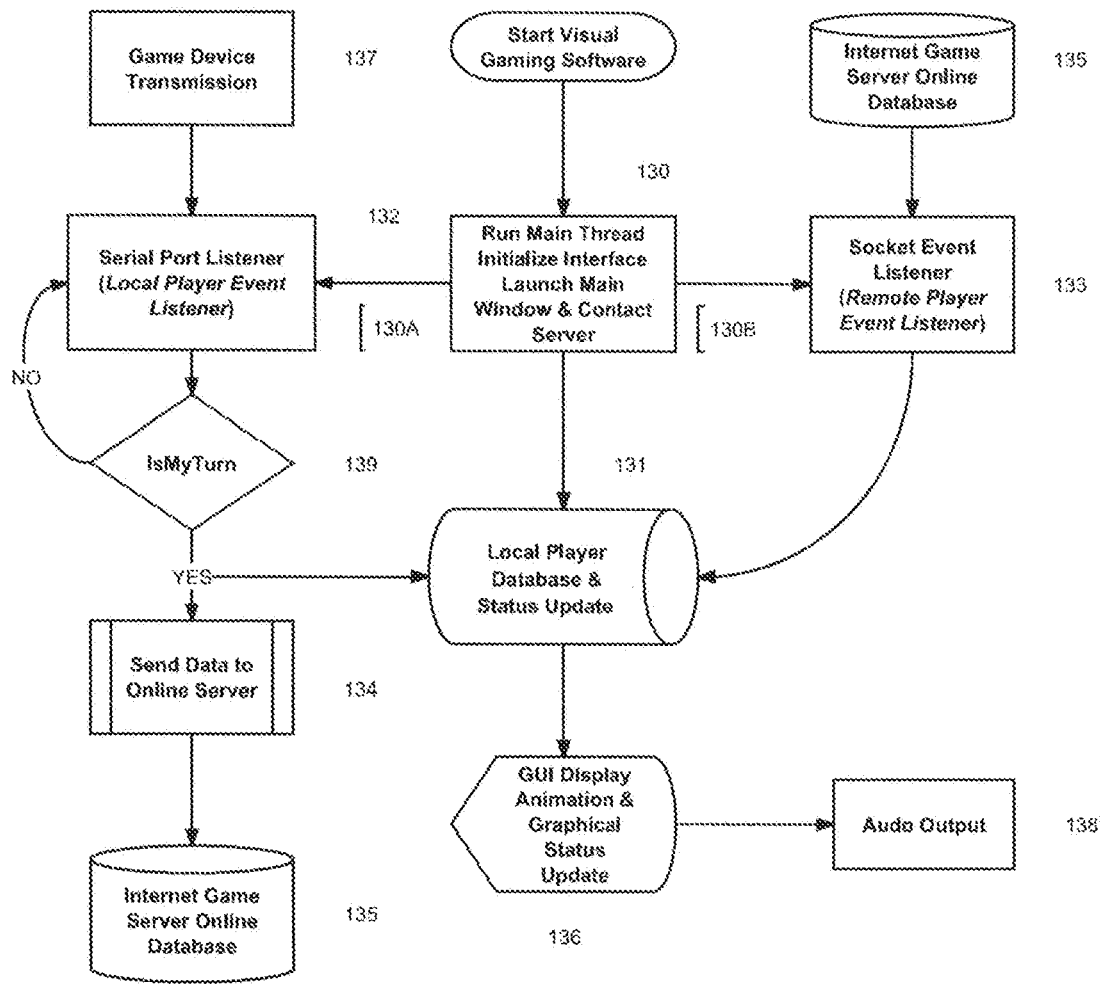
FIG. 11 is a functional block diagram of the software operation of the computer of FIG. 10.

At each remote player site, the computer 28 (FIG. 1) under the control of the golfing software program (shown in the golfing software system functional block diagram, FIG. 11) monitors and controls initialization and the sequential play of the golf game, or alternatively, the individual player practice session. Upon startup by a player at a particular site, the system input parameters are set and the system internet and player port interfaces are initialized 130 as indicated by the arrows 130A and 130B. For internet communications, the serial port listener of the computer 28 is enabled in the preferred embodiment and a remote player event listener is initialized. It will communicate events from one or more of the smart golf club, the golf ball receptacle and the motion sensor plate. The main operational software (program) thread is run 130, and the system awaits data input from the appropriate computer communications ports at 132 (port), 133 (Remote player Socket Event Listener).

Figure 12:
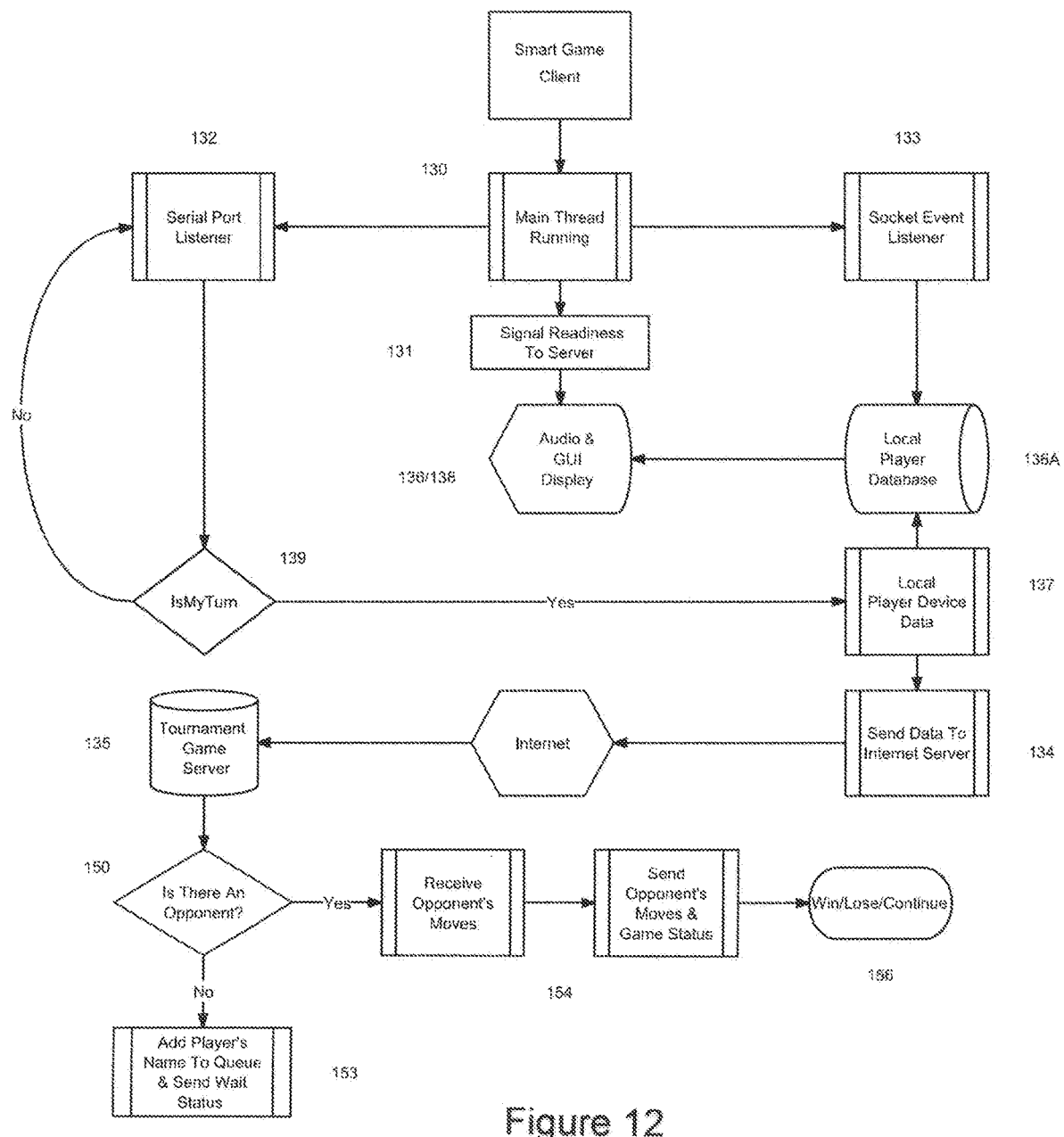
FIG. 12 is a flowchart illustrative of a client-server portion of the operation of the computer of FIG. 10 operating as indicated in the block diagram of FIG. 11.

If the competitive play mode has been selected, the program generates a player participation request and sends 134 the request to the game internet server (GGC server) 34 (FIG. 1). Upon identification of a player opponent at 150 (FIG. 12) by the game server, the program initiates the player identification sequence 152 and sequential play begins 154. This software sequence and control routine occurs at each remote site where play has been initiated. During the game play sequences 154, the program generates the appropriate animation, display, and audio data and commands 136 and 138 (FIG. 11), and communicates with the associated display and speaker devices 30 and 31 (FIG. 1). Upon the occurrence of a local player event detected at 133, the main operating program at 130 displays the event at 136, and communicates the event at 132 by causing a device transmission at 137 to be sent at 134 via the internet game server 135 which displays the event for the opposing player and alerts the opposing player that it is his/her turn to play. The local player event may be, but is not limited to, the smart golf club impacting a ball, the swing of a club across the sensing plate or the ball's entry into the receptacle. The program contains time delay limits for the player action, and delays of play beyond these limits generate play quit and disconnect signals.

The event at 133 also has the effect of indicating at 139 that it is no longer the local player's turn and enables (as indicated by line 139) the serial port listener at 132 to detect an event from the remote player, again via the internet.

If the single player practice mode is selected, the internet communications sequences are disabled, other software sequential operating routines continue as above described, and the player's golf club stroke, ball-receptacle contact, and/or club swing motion sensor information are communicated only to the computer located at the player's site and the performance information analyzed and displayed only at the local player's site.

When a game is won, lost loco, or terminated, the gaming software system generates the appropriate output signals 156 (FIG. 12), displays the player performance information, and resets to initial pre-game conditions. If one player opponent quits the game or is "timed out" (due to an excessive delay in play) and the remaining player wishes to continue play, the software resumes an internet search for another opponent 152 and 153.

Using programming as contained in the accompanying microfiche appendix, one skilled in the art can readily accomplish the game programming described. Alternative programming too will be apparent from the foregoing functional description and the illustrations contained in the appended drawings While a preferred embodiment has been described, it will be appreciated that many variations and modifications in the system, its operation, and its various components may be made without departure from the spirit and scope of invention as set forth in the appended claims.

What is claimed is:

1. A competitive play system, comprising:
a computer with a wireless receiver, the computer to receive digitally coded radio frequency transmissions from a plurality of golfers; and
a golf club, comprising:
a club head;
a shaft;
a microcontroller, pre-programmed with identification information corresponding to the golf club;
a wireless communication transmitter, in communication with the wireless receiver of the computer;
an electrical contact sensor, electrically coupled to the microcontroller and attached to the club head; and
a power source,
wherein the microcontroller is further programmed to receive one-stroke impact data from the electrical contact sensor, and transmit to the computer, the one-stroke impact data of at least one of a game projectile and/or a sports equipment item during a swing of a user.

2. The system of claim 1, wherein the wireless communication transmitter transmits via a wireless radio frequency communications protocol.

3. The system of claim 1, further comprising:
a plurality of contact and/or noncontact sensors.

4. The system of claim 3, further comprising:
a motion detector.

5. The system of claim 3, further comprising:
a proximity detector.

6. The system of claim 3, further comprising:
an accelerometer, configured to derive spatial acceleration motion data of the golf club.

7. The system of claim 3, further comprising:
a gyro meter, configured to derive spatial orientation motion data of the golf club.

8. The system of claim 1, wherein the electrical contact sensor comprises piezoelectric and/or piezoresistive sensors.

9. The system of claim 1, wherein the electrical contact sensor measures one-stroke data from impact by at least one of a golf ball and a sports equipment item.

10. The system of claim 1, wherein the microcontroller is further configured to determine if impact occurs between the golf club and the sports equipment item comprising a golf ball.

11. The system of claim 1, wherein the microcontroller indicates a location of impact on a clubface of the golf club head of the golf ball.

12. The system of claim 1, further comprising:
a wireless communication receiver to receive communications data.

13. The system of claim 1, wherein the electrical contact sensor is configured to transmit force data indicative of a force of impact between the golf ball and the golf club, and a time.

14. The golf club system of claim 1, wherein the microcontroller, the wireless communication transmitter, the electrical contact sensor, and the power source are retrofitted on a standard golf club comprising the club head and the shaft.

15. A computer-implemented system, comprising:
a sports implement, configured to be manipulated by a player during a game;
a display screen;
an electrical contact sensor, disposed on the sports implement;
a wireless communication interface to communicatively coupled the sports implement and the display screen;
a first computer;
a second computer; and
a game server,
wherein the wireless communication interface is configured to transmit sensor data to the first computer, the first computer configured to receive sensor data from the electrical contact sensor, the first computer is further configured to process the electrical contact sensor data and transmit the electrical contact sensor data to the second computer, and the second computer is configured to transmit the electrical contact sensor data received from the first computer to the game server via a data communication network.

16. The system of claim 15, wherein the second computer is operatively coupled to the display screen, and the second computer creating an animated first visual event simulation from the electrical contact data acquired from the first computer for display on the display screen.

17. The system of claim 15, wherein the wireless communication link interface uses a radio frequency communication protocol.

18. The system of claim 15, further comprising
a proximity detector.

19. The system of claim 15, further comprising:
an accelerometer, configured to derive spatial acceleration motion data of the sports implement.

20. The system of claim 15 further comprising:
a gyro meter, configured to derive spatial orientation motion data of the sports implement.

* * * * *